(12) United States Patent
Yoda

(10) Patent No.: US 12,239,848 B2
(45) Date of Patent: Mar. 4, 2025

(54) BED CALCULATION WITH ISOTOXIC PLANNING

(71) Applicant: Elekta, Inc., Atlanta, GA (US)

(72) Inventor: Kiyoshi Yoda, Hyogo (JP)

(73) Assignee: Elekta, Inc., Atlanta, GA (US)

( * ) Notice: Subject to any disclaimer, the term of this patent is extended or adjusted under 35 U.S.C. 154(b) by 477 days.

(21) Appl. No.: 17/647,968

(22) Filed: Jan. 13, 2022

(65) Prior Publication Data

US 2023/0218926 A1    Jul. 13, 2023

(51) Int. Cl.
*A61N 5/10*        (2006.01)
*G16H 20/40*       (2018.01)
*G16H 50/20*       (2018.01)

(52) U.S. Cl.
CPC ......... *A61N 5/1038* (2013.01); *A61N 5/1031* (2013.01); *G16H 20/40* (2018.01); *G16H 50/20* (2018.01); *A61N 5/1084* (2013.01)

(58) Field of Classification Search
CPC .. A61N 5/1038; A61N 5/1031; A61N 5/1084; G16H 20/40; G16H 50/20; G16H 50/70
See application file for complete search history.

(56) References Cited

U.S. PATENT DOCUMENTS

| | | | | |
|---|---|---|---|---|
| 9,764,162 B1* | 9/2017 | Willcut | ................ | G06T 7/0014 |
| 2019/0030370 A1* | 1/2019 | Hibbard | ............... | A61N 5/1067 |
| 2020/0179720 A1* | 6/2020 | Scott | ...................... | A61N 5/103 |
| 2021/0052916 A1 | 2/2021 | Isola | | |
| 2022/0126116 A1* | 4/2022 | Harrer | ................. | A61N 5/1031 |
| 2023/0144124 A1* | 5/2023 | Turner | .................. | G16H 20/40 600/427 |
| 2023/0389856 A1* | 12/2023 | Heasman | ............... | A61B 5/369 |

OTHER PUBLICATIONS

Fowler, John F., "The linear-quadratic formula and progress in fractionated radiotherapy", The British journal of radiology 62.740, (1989), 679-694.

Wang, Jian Z., "How low is the a ß ratio for prostate cancer?", International Journal of Radiation Oncology* Biology* Physics 55.1, (2003), 194-203.

* cited by examiner

*Primary Examiner* — Dhaval V Patel
(74) *Attorney, Agent, or Firm* — Schwegman Lundberg & Woessner, P.A.

(57) ABSTRACT

Systems and methods are disclosed for performing operations comprising: receiving dose information representing dose delivered during a first radiotherapy treatment fraction; accessing one or more previous dose information representing dose delivered during one or more previous radiotherapy treatment fractions; computing a measure of biologically effective dose (BED) based on a combination of the dose information delivered during a first radiotherapy treatment fraction and the dose delivered during the one or more previous radiotherapy treatment fractions; and performing an isotoxic planning process for delivering a second radiotherapy treatment fraction following the first radiotherapy treatment fraction based on the computed measure of BED.

28 Claims, 12 Drawing Sheets

BED CALCULATION WITH ISOTOXIC PLANNING

TECHNICAL FIELD

Embodiments of the present disclosure pertain generally to performing isotoxic planning in radiotherapy treatment sessions.

BACKGROUND

Radiation therapy (or "radiotherapy") can be used to treat cancers or other ailments in mammalian (e.g., human and animal) tissue. One such radiotherapy technique involves irradiation with a Gamma Knife, whereby a patient is irradiated by a large number of low-intensity gamma ray beams that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively, or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Overview

In some aspects, systems and methods are provided for performing operations including: receiving dose information representing delivery of a dose distribution to a target corresponding to a first radiotherapy treatment fraction; determining a target type associated with the target; applying a machine learning technique, associated with the determined target type, to the dose information to predict a measure of biologically effective dose (BED), the machine learning technique being trained to establish a relationship between a set of prior dose distributions delivered for the target type and one or more ground truth BED measurements; and performing an isotoxic planning process based on the predicted measure of BED.

In some aspects, the operations further comprise: storing a plurality of machine learning techniques each associated with a different target type and configured to predict BED for the associated target type.

In some aspects, the operations further comprise selecting the machine learning technique from the plurality of machine learning techniques based on the determined target type.

In some aspects, the operations further comprise: computing a measured BED by: accumulating a plurality of doses delivered across a plurality of radiotherapy treatment fractions into a first value, the plurality of radiotherapy treatment fractions comprising the first radiotherapy treatment fraction; accumulating an adjusted sum of squares of the plurality of doses; and combining the accumulated plurality of doses and the adjusted sum of squares of the plurality of doses into the measure of BED; and comparing the measured BED to the predicted measure of BED.

In some aspects, the operations further comprise: computing a difference between the measured BED to the predicted measure of BED; comparing the difference to a threshold; and controlling delivery of a radiotherapy treatment plan based on a result of comparing the difference to the threshold.

In some aspects, the operations further comprise training the machine learning technique by: obtaining a set of training data comprising a set of training dose distributions and a ground truth measure of BED; applying the machine learning technique to the set of training dose distributions to predict a training measure of BED; computing a deviation between the predicted training measure of BED and the ground truth measure of BED; and updating one or more parameters of the machine learning technique based on the deviation.

In some aspects, the set of training data is generated by: obtaining the set of training dose distributions associated with multiple radiotherapy treatment fractions; accumulating the set of training dose distributions into a first value; accumulating an adjusted sum of squares of the set of training dose distributions; combining the accumulated set of training dose distributions and the adjusted sum of squares of the set of training dose distributions into the ground truth measure of BED; and associating the ground truth measure of BED with the set of training dose distributions.

In some aspects, systems and methods are provided for performing operations comprising: receiving dose information representing dose delivered during a first radiotherapy treatment fraction; accessing one or more previous dose information representing dose delivered during one or more previous radiotherapy treatment fractions; computing a measure of biologically effective dose (BED) based on a combination of the dose information delivered during a first radiotherapy treatment fraction and the dose delivered during the one or more previous radiotherapy treatment fractions; and performing an isotoxic planning process for delivering a second radiotherapy treatment fraction following the first radiotherapy treatment fraction based on the computed measure of BED.

In some aspects, the one or more previous radiotherapy treatment fractions were delivered prior to the first radiotherapy treatment fraction.

In some aspects, the operations further comprise: computing a total survival fraction of tumor cells based on the computed measure of BED.

In some aspects, the operations further comprise: obtaining a first constant corresponding to a tumor cell associated with a patient being treated by the first radiotherapy treatment fraction; and computing the total survival fraction as an exponential of the first constant and the computed measure of BED.

In some aspects, the operations further comprise: accumulating a plurality of doses delivered across a plurality of radiotherapy treatment fractions into a first value, the plurality of radiotherapy treatment fractions comprising the first radiotherapy treatment fraction and the one or more previous radiotherapy treatment fractions; accumulating an adjusted sum of squares of the plurality of doses; and combining the accumulated plurality of doses and the adjusted sum of squares of the plurality of doses into the measure of BED.

In some aspects, the operations further comprise: obtaining first and second constants corresponding to a tumor cell associated with a patient being treated by the first radiotherapy treatment fraction; computing a ratio of the first and second constants; and multiplying the sum of squares of the plurality of doses by the ratio to compute the adjusted sum of squares of the plurality of doses.

In some aspects, the operations further comprise: presenting the measure of BED to an operator before delivery of the second radiotherapy treatment fraction.

In some aspects, the operations further comprise: receiving magnetic resonance imaging information associated with the second radiotherapy treatment fraction prior to delivery of the second radiotherapy treatment fraction; computing, based on the magnetic resonance imaging information, a distance between a critical organ and a tumor cell associated with a patient being treated by the second radiotherapy treatment fraction; and setting a dose to be delivered during the second radiotherapy treatment fraction based on the distance and the measure of BED.

In some aspects, the operations further comprise: adjusting the set dose during delivery of the second radiotherapy treatment fraction; and updating the measure of BED based on the adjusted set dose delivered during the second radiotherapy treatment fraction.

In some aspects, the measure of the BED comprises a second order function of a plurality of doses delivered across a plurality of radiotherapy treatment fractions.

In some aspects, the measure of the BED is computed in accordance with: $BED=\Sigma d_i+(\beta/\alpha)\Sigma d_i^2$ where BED is the measure of BED, $d_i$ represents dose delivered during a radiotherapy treatment fraction number i, $\beta$ and $\alpha$ represent respectively first and second constants associated with a tumor cell associated with a patient being treated by the first radiotherapy treatment fraction.

In some aspects, a total survival fraction is computed in accordance with: $\exp[-\alpha\{BED\}]$ where exp is an exponential function.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
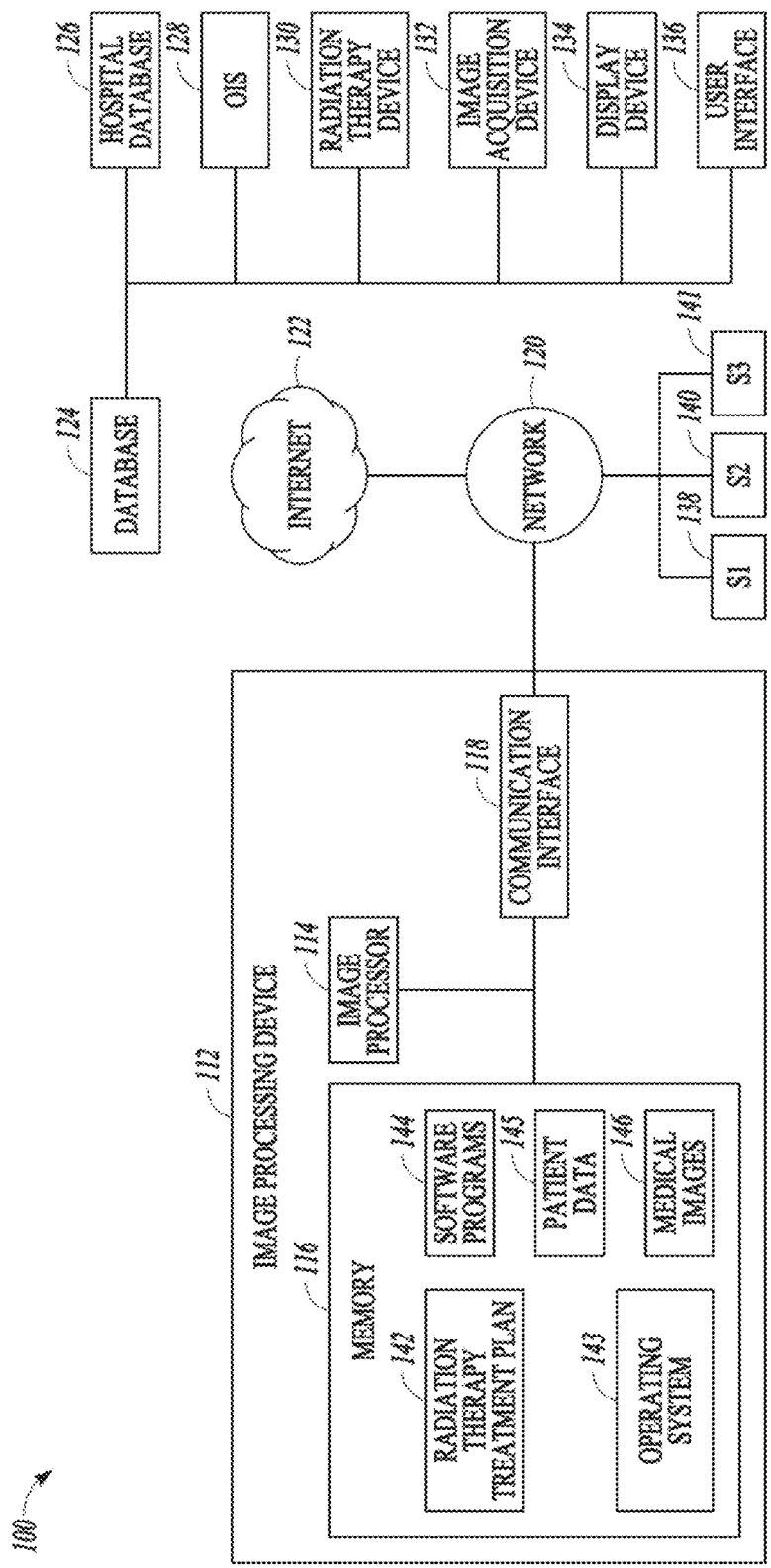
FIG. 1 illustrates an example radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not be taken in a limiting sense, and the scope of the present disclosure is defined by the appended claims and their equivalents.

Typical radiotherapy treatment sessions rely on MR images (MRI) to visualize very small tumor cells. To treat such small tumor cells, the radiotherapy dose per day or fraction can be increased which consequently decreases the number of times a patient has to undergo radiotherapy treatment (e.g., reduce the number of radiotherapy treatment sessions). The drawback of increasing the dose per day or fraction is the potential harm to nearby critical organs. Given that such nearby organs and/or tumor move from one day to the next, the MRI images can be captured just before or during a radiotherapy treatment fraction in order to adjust (increase or decrease) the amount of radiotherapy dose to the tumor that is being or will be delivered in the given radiotherapy treatment session. In some cases, where the distance between the tumor cells and critical organs is small, the radiotherapy dose to the tumor can be decreased while keeping the dose to nearby critical organs or OARs unchanged, and where the distance between the tumor cells and critical organs is relatively large, the radiotherapy dose to the tumor can be increased by keeping the dose to nearby critical organs or OARs identical. This process of modifying the radiotherapy dose distribution relative to the prescribed radiotherapy dose distribution specified in a radiotherapy treatment plan is referred to as isotoxic planning. Namely, isotoxic planning involves an automated or operator guided radiotherapy dose distribution adjustment based on MR or even CT images captured just prior or during a given radiotherapy treatment fraction based on a distance between a tumor cell and a critical organ, in order to maximize allowable dose to the tumor while giving the same radiation toxicity to the nearby critical organs in each treatment delivery or fraction Certain isotoxic planning techniques (or isoeffective dose calculations) can utilize a BED measure. Specifically, the BED represents the efficiency at which cancer cells are killed with radiation or radiotherapy, such that when the BED is increased, the cancer cells are killed more efficiently with improved survival rates. The BED is indicative of how much radiotherapy dose was applied to the tumor cells rather than the actual physical radiotherapy dose distribution that was delivered by the radiotherapy treatment device. In this way, the BED is a measure of the true biological dose delivered by a particular combination of dose per fraction and total dose to a particular tissue characterized by a specific constant associated with a type of tumor cell. The BED is the amount of an absorbed radiation that reaches targets or sites of action within the body to cause a biologic effect.

The traditional BED formula that is typically computed to represent the cancer cell destruction presumes isoeffective planning whereby the dose to the tumor remains constant for all the treatment fractions. In other words, if we employ the traditional BED formula for isotoxic planning, an approximation or mean of the radiotherapy dose to the tumor needs to be used to calculate the BED. Such an approximation or mean, though, can result in quadratically inaccurate representations of the BED. This can severely impact the isotoxic planning and can end up causing inaccurate BED calculation. Because the BED directly and theoretically relates to cancer cells' survival rates, inaccuracy in the BED may result in incorrect cancer research outcomes after collecting a large number of clinical data including the relationship between the BED and treatment outcome (overall survival, local control etc) for each patient.

The disclosed embodiments provide an advanced technique for accurately computing and measuring BED based on an accumulation of dose delivered during a current radiotherapy treatment fraction and the dose delivered during one or more prior radiotherapy treatment fractions. Based on the improved measure of the BED, a more accurate representation is provided of the amount of dose distribution delivered to the cancer cells in a patient. This more accurate BED measure can be used to perform an isotoxic planning process. In some implementations, a plurality of doses delivered across a plurality of radiotherapy treatment fractions is accumulated into a first value. A quadratic term of the plurality of doses is additionally accumulated and combined with the accumulated plurality of doses to generate the measure of BED. In some implementations, a total survival fraction of tumor cells can also be computed based on the measure of BED.

In this way, the accuracy of the BED delivered to the tumor of a patient over entire radiotherapy treatment fractions can be improved which can provide more accurate prediction of the patient's treatment outcome.

FIG. 1 illustrates an example radiotherapy system 100 for providing radiation therapy to a patient, according to some embodiments. The radiotherapy system 100 includes an image processing device 112 (also referred to as a dose processing device). The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114.

In some embodiments, the software programs 144 may convert medical images of one format MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the trained predictive model may convert a CT image into an MRL image. In other embodiments, the software programs 144 may register the patient image (e.g., a CT image or an MR image) with that patient's dose distribution (also represented as an image) so that corresponding image voxels and dose voxels are associated appropriately by the network. In yet other embodiments, the software programs 144 may substitute functions of the patient images or processed versions of the images that emphasize some aspect of the image information. Such functions might emphasize edges or differences in voxel textures, or any other structural aspect useful to neural network learning. In other embodiments, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In some embodiments, the software programs 144 can compute BED for a particular patient and/or type of tumor cell being treated in a radiotherapy treatment session. Specifically, the software programs 144 receive dose information representing dose distribution delivered during a first radiotherapy treatment fraction. The software programs 144 access one or more previous dose information representing dose distribution delivered during one or more previous radiotherapy treatment fractions. The software programs 144 compute a measure of BED based on a combination of the dose information delivered during a first radiotherapy treatment fraction and the dose delivered during the one or more previous radiotherapy treatment fractions. For example, the software programs 144 can compute the BED in accordance with Equation 1 below:

$$BED = \Sigma d_i + (\beta/\alpha) \Sigma d_i^2 \quad \text{Equation 1}$$

where BED is the measure of BED, $d_i$ represents dose delivered during a radiotherapy treatment fraction number i, $\beta$ and $\alpha$ represent respectively first and second constants associated with a tumor cell associated with a patient being treated by the first radiotherapy treatment fraction with isotoxic planning, whereby the dose to nearby critical organs is predetermined by a radiation oncologist according to published literatures.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed b image processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. The medical images 146 may include or be associated with metadata that specifies estimated motion, such as the periodic motion phase of a target region depicted in the medical images 146 (e.g., the respiratory phase of a breathing cycle depicted in the medical images 146). Such estimated motion for the medical images can be generated or computed by a trained ML model and/or by performing some image registration techniques or processes on the medical images. Patient data 145 may include information such as (1) functional organ modeling data (e.g., serial versus parallel organs, appropriate dose response models, etc.); (2) radiation dosage data (e.g., DVH information); (3) other clinical information about the patient and course of treatment (e.g., other surgeries, chemotherapy, previous radiotherapy, etc.); (4) type of tumor cells being treated by the radiotherapy treatment session. The medical images 146 may be received from or be associated with a device that measures or determines a motion phase of periodic motion (e.g., estimated motion) of a target region depicted in the images.

In addition, the processor 114 may utilize software programs to generate intermediate data such as updated parameters to be used, for example, by a machine learning model, such as a neural network model; or generate intermediate 2D or 3D images, which may then subsequently be stored in memory device 116. The processor 114 may subsequently transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image such software programs144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP). a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesia® family manufactured by Nvidia™, GMA, Iris™ family manufactured by Inel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory device 116, to perform various operations, processes, methods that will he explained in greater detail below.

The memory device 116 can store medical images 146. In some embodiments, the medical images 146 may include one or more MRI images (e.g., 2D 3D MRI, 2D streaming MRI, four-dimensional (4D) MRI, 4D volumetric MRI, 4D cine MRI, etc.), functional MRI images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer-generated synthetic images (e.g., pseudo-CT images), aperture images, graphical aperture image representations of MLC leaf positions at different gantry angles, and the like. Further, the medical images 146 may also include medical image data, for instance, training images, ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the image processing device 112 may use to perform operations consistent with the disclosed embodiments.

The memory device 115 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that is executable by the processor 114. For example, the memory device 116 may store one or more radiation therapy treatment plans 142.

The image processing device 112 can communicate with the network 120 via the communication interface 118, which can be communicatively coupled to the processor 114 and the memory device 116. The communication interface 118 may provide communication connections between the image processing device 112 and radiotherapy system 100 components (e.g., permitting, the exchange of data with external devices). For instance, the communication interface 118 may, in some embodiments, have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include a plurality of devices located either in a central or a distributed mariner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories and optical and magnetic media. For example, the processor-readable storage medium can be one or more volatile, transitory, non-transitory, or non-volatile tangible computer-readable media Image processor 114 may communicate with database 124 to read images into memory device 116 or store images from memory device 116 to database 124. For example, the database 124 may be configured to store a plurality of images (e.g., 3D MRL 4D MRI, 2D MRI slice images, CT images, 2D Fluoroscopy images, X-ray images, raw data from MR scans or CT scans, Digital Imaging and Communications in Medicine (DICOM) data, projection images, graphical aperture images, etc.) that the database 124 received from image acquisition device 132. Database 124 may store data to be used by the image processor 114 when executing software program 144 or when creating radiation therapy treatment plans 142. Database 124 may store the data produced by the trained machine learning mode, such as a neural network including the network parameters constituting the model learned by the network and the resulting estimated data. As referred to herein, "estimate" or "estimated" can be used interchangeably with "predict" or "predicted" and should be understood to have the same meaning. The image processing device 112 may receive the imaging data, such as a medical image 146 (e.g., 2D MRI slice images, CT images, 2D Fluoroscopy images, X-ray images, 3DMRI images, 4D MRI images, projection images, graphical aperture images, image contours, etc.) from the database 124, the radiation therapy device 130 (e.g., an MR-linac), and/or the image acquisition device 132 to generate a treatment plan 142. The image data that is received can be associated with estimated motion of each image. The estimated motion can be received together with the images and/or can be computed upon receipt of the images. In some examples, a distance between a target (e.g., tumor cells) and one or more critical organs can be measured based on the images received from the image acquisition device 132. This distance, together with a computed BED, can be used to perform isotoxic planning for one or more radiotherapy treatment fractions delivered to the patient associated with the images.

In an embodiment, the radiotherapy system 100 can include an image acquisition device 132 that can acquire medical images (e.g., MRI images, 3D MRI, 2D streaming MRI, 4D volumetric MRI, CT images, cone-Beam CT, PET images, functional MRI images (e.g., fMRI, DCE-MRI and diffusion MRI). X-ray images, fluoroscopic image, ultrasound images, radiotherapy portal images, SPECT images, and the like) of the patient. mage acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can be also stored by the image processing device 112, as medical image 146 in memory device 116. In some cases, the image acquisition device 132 can generate or provide estimated motion for each image or group of images captured by the image acquisition device 132.

In some embodiments, the image acquisition device 132 may be integrated with the radiation therapy device 130 as a single apparatus (e.g., an MR-linac). Such an MR-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In some embodiments, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment.

The image processing device 112 may generate and store radiation therapy treatment plans 142 for one or more patients. The radiation therapy treatment plans 142 may provide information about a particular radiation dose (or dose distribution) to be applied to each patient at each radiotherapy treatment fraction. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target such as a tumor, to generate contours of the images. In some embodiments, the delineation of one or more OARs, such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained and used to generate a contour of the image. Contours of the image can include data overlaid on top of the image that delineates one or more structures of the anatomy. In some cases, the contours can be files associated with respective images that specify the coordinates or 2D or 3D locations of various structures of the anatomy depicted in the images.

In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, a computed measure of BED, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor: defining that the spinal cord, brain stem, and optic structures receive ≤45 Gy, ≤55 Gy and <54 Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (,e.g., projection images, graphical aperture images, contours, dosages, beam angles, etc.) treatment plans, a measure of BED, a target, localizing a target and/or tracking a target, or any related information to the user. The user interface 136 may be a keyboard, a keypad, a touch screen or any type of device that a user may use to input information to radiotherapy system 100. Alternatively, the display device 134 and the user interface 136 may be integrated into a device such as a tablet computer (e.g., Apple iPad®, Lenovo ThinkPad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory and computational capability available, the entire radiotherapy system 10 could be implemented as a virtual machine.

Figure 2A:
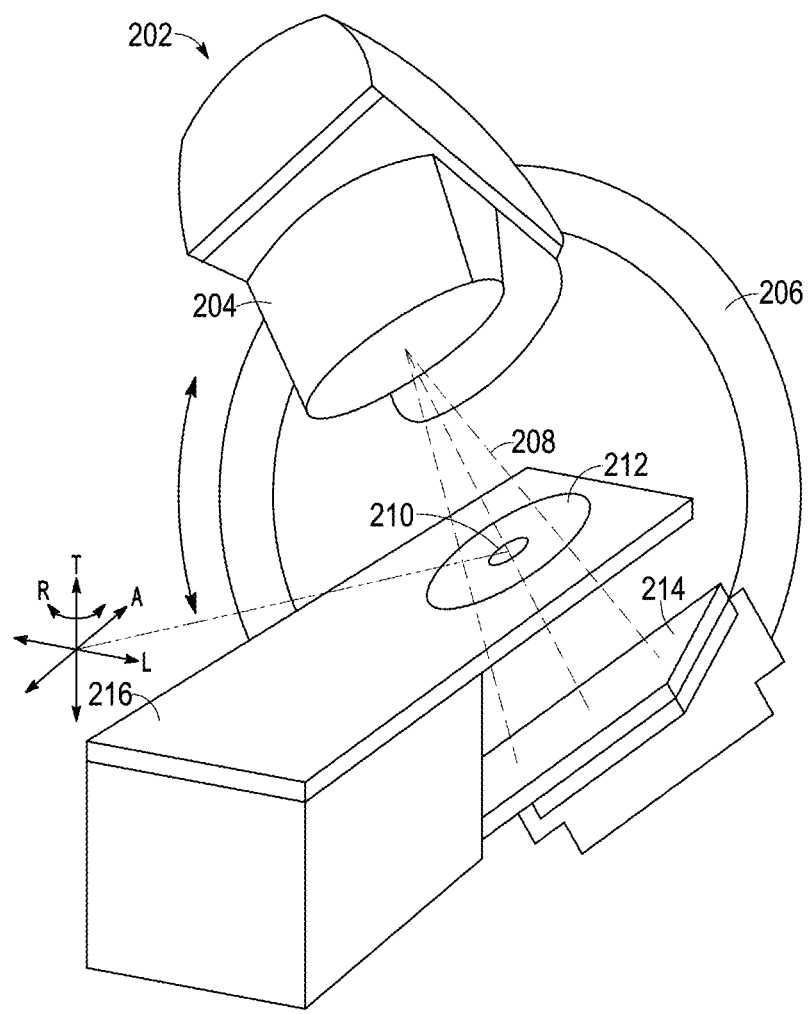
FIG. 2A illustrates an example radiation therapy system that can include radiation therapy output configured to provide a therapy beam, according to some embodiments of the present disclosure.

FIG. 2A illustrates an example radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC as described in the illustrative embodiment of FIG. 5, below.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch's 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can precisely target the tumor. The MLC may be integrated and included within gantry 206 to deliver the radiation beam 208 of a certain shape.

The coordinate system (including axes A, T, and L) shown in FIG. 2A can have an origin located at an isocenter 210. The isocenter 210 can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an embodiment, the imaging detector 214 can be located within a field of the therapy beam 208.

The imaging detector 214 can be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within system 100 or remote from it.

In an illustrative embodiment, one or inure of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations. or locations of the gantry 206, couch 216, or therapy output 204. The therapy deliveries can occur sequentially, but can intersect in a desired therapy locus on or within the patient, such as at the isocenter 210 A prescribed cumulative dose of radiation therapy can thereby be delivered to the therapy locus while damage to tissue near the therapy locus can be reduced or avoided.

Figure 2B:
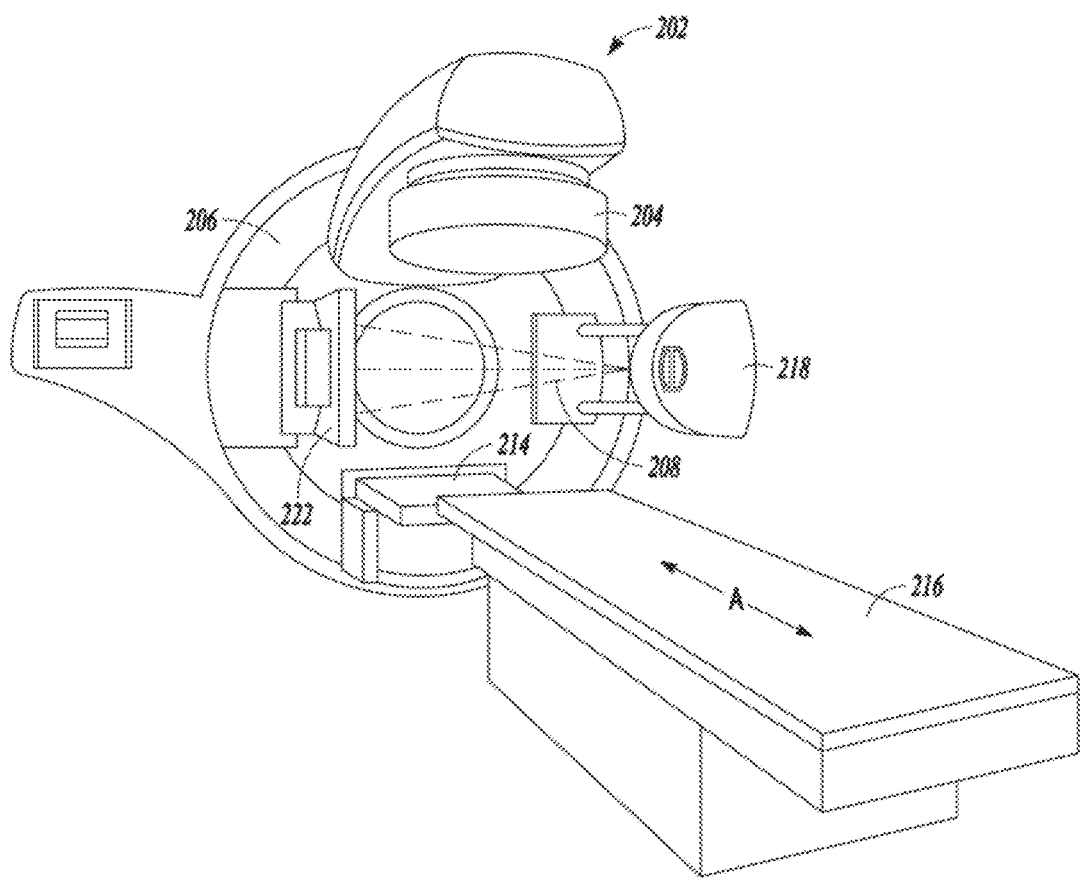
FIG. 2B illustrates an example system including a combined radiation therapy system and an imaging system, such as a cone beam computed tomography (CBCT) imaging system, according to some embodiments of the present disclosure.

FIG. 2B illustrates an example radiation therapy device 202 that may include a combined lilac and an imaging system, such as can include a CT imaging system. The radiation therapy device 202 can include an MLC (not shown). The CT imaging system can include an imaging X-ray source 218, such as providing X-ray energy in a kilo electron-Volt (keV) energy range. The imaging X-ray source 218 can provide a fan-shaped and/or a conical beam 208 directed to an imaging detector 222, such as a fiat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively lower-energy X-ray diagnostic beam, for imaging.

In the illustrative embodiment of FIG. 2B, the radiation therapy output 204 and the X-ray source 218 can be mounted on the same rotating gantry 206, rotationally separated from each other by 90 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
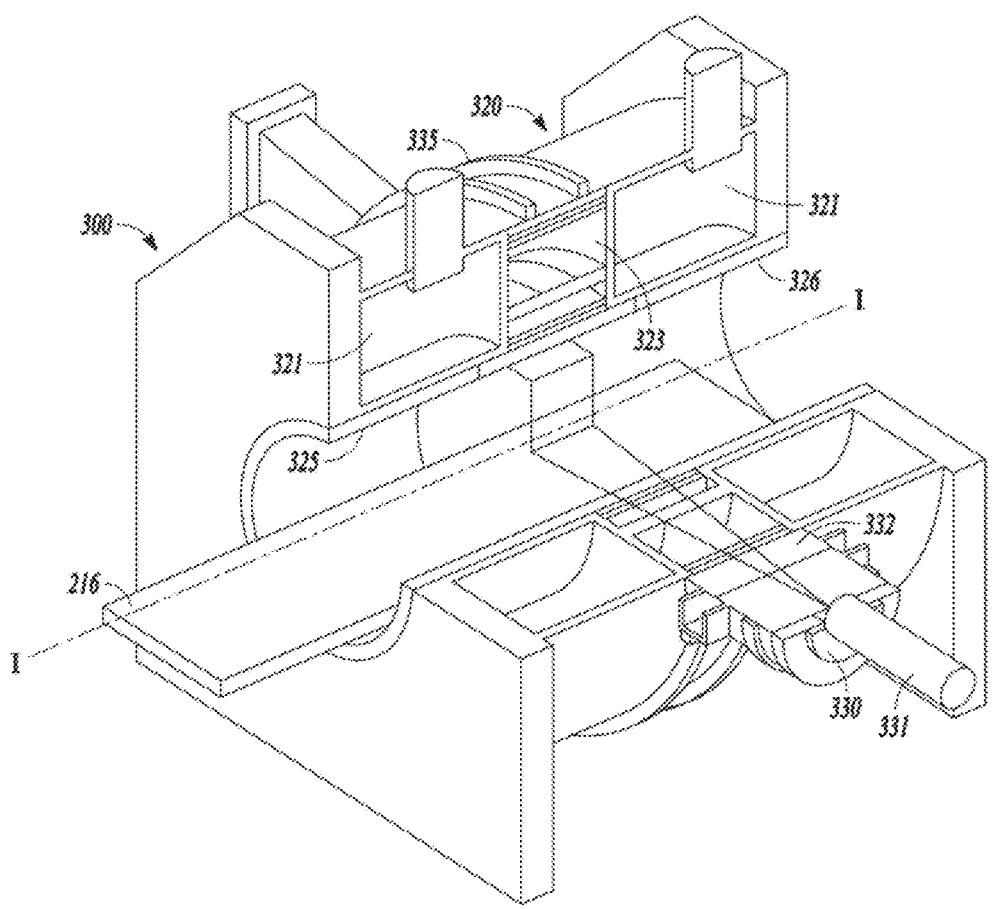
FIG. 3 illustrates a partially cut-away view of an example system including a combined radiation therapy system and an imaging system, such as an MR imaging (MRI) system, according to some embodiments of the present disclosure.
Figure 4A:
FIGS. 4A and 4B are images depicting differences between an example MRI image and a corresponding CT image, respectively, according to some embodiments of the present disclosure.
Figure 4B:
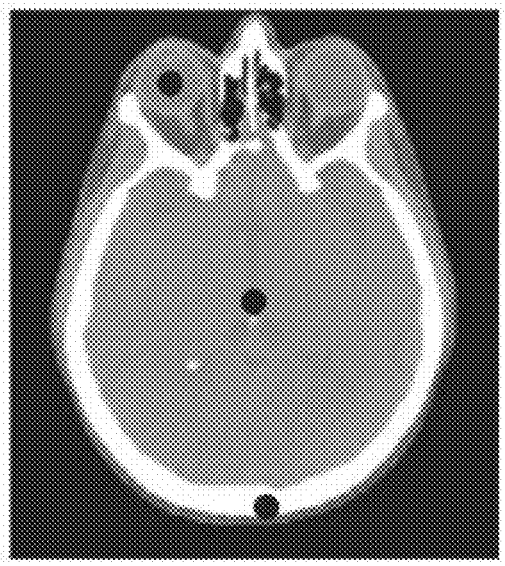

FIG. 3 depicts an example radiation therapy system 300 that can include combining a radiation therapy device 202 and an imaging system, such as an MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first imaging modality MRI image shown in FIG. 4A) or destination images of a second imaging modality (e.g., CT image shown in FIG. 4B).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In embodiments where magnet 321 can also include a central window 323 between coils 325 and 326, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Figure 5:
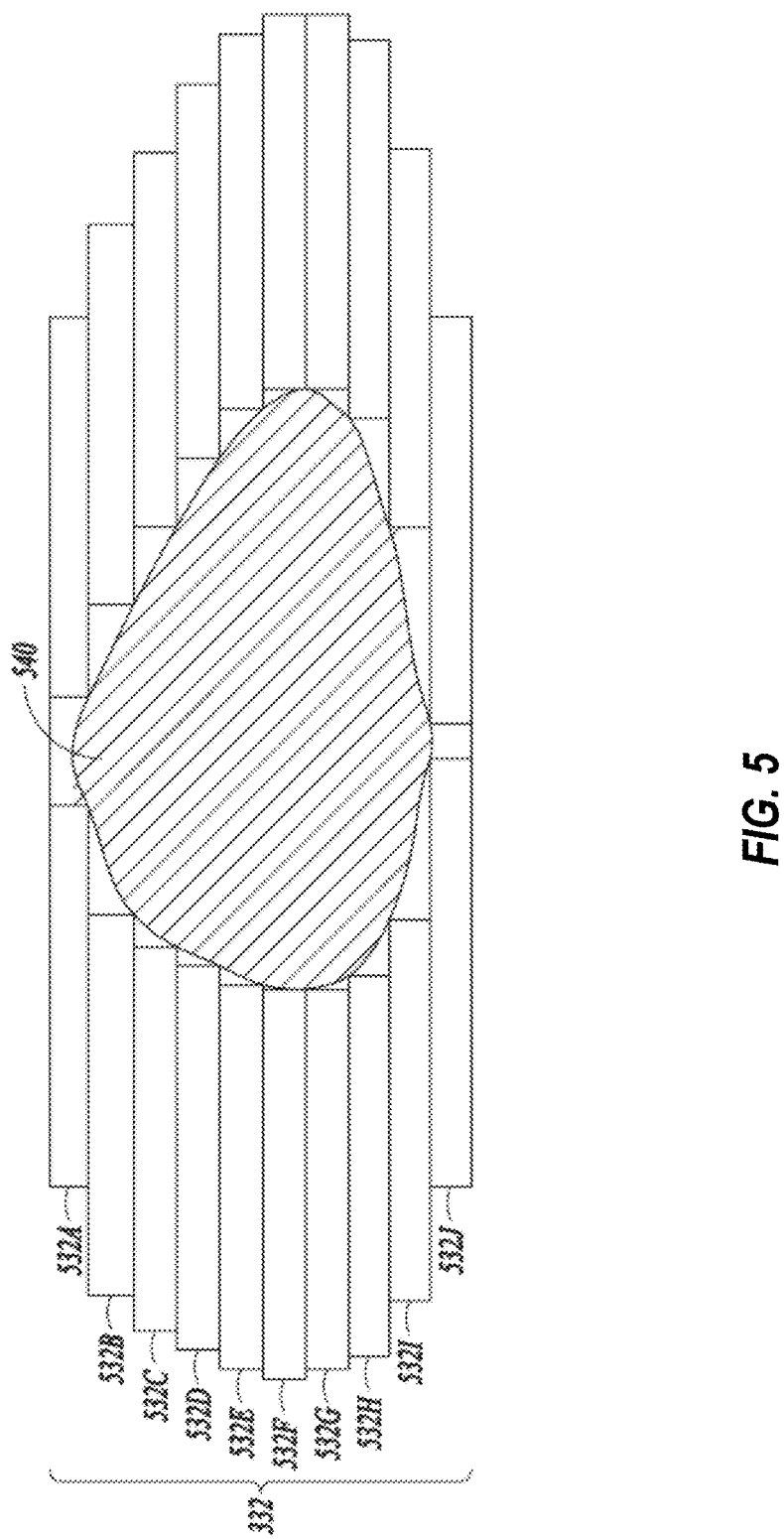
FIG. 5 illustrates an example collimator configuration for shaping, directing, or modulating an intensity of a radiation therapy beam, according to some embodiments of the present disclosure.

Radiotherapy device 330 may include the radiation source 331, such as an X-ray source or a linac, and an MLC 332 (shown below in FIG. 5). Radiotherapy device 330 may be mourned on a chassis 335. One or more chassis motors (not shown) may rotate chassis 335 around couch 216 when couch 216 is inserted into the treatment area. In an embodiment, chassis 335 may be continuously rotatable around couch 216, when couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnet 321, coils 325 and 326, and chassis 335. Control circuitry may then control radiation source 331, MLC 332, and the chassis motors) to deliver radiation to the patient through the window between coils 325 and 326 according to a radiotherapy treatment plan.

FIG. 2A, FIG. 2B, and FIG. 3 illustrate generally embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In another embodiment, the therapy output can be fixed, such as located in a region laterally separated from the patient, and a platform supporting the patient can be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient. FIG. 5 illustrates an example MLC 332 that includes leaves 532A through 532J that can be automatically positioned to define an aperture approximating ii tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction and having ends oriented orthogonally to the beam direction (as shown m the plane of the illustration of FIG. 2A). A "state" of the MLC 332 can be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as IMRT.

Figure 6:
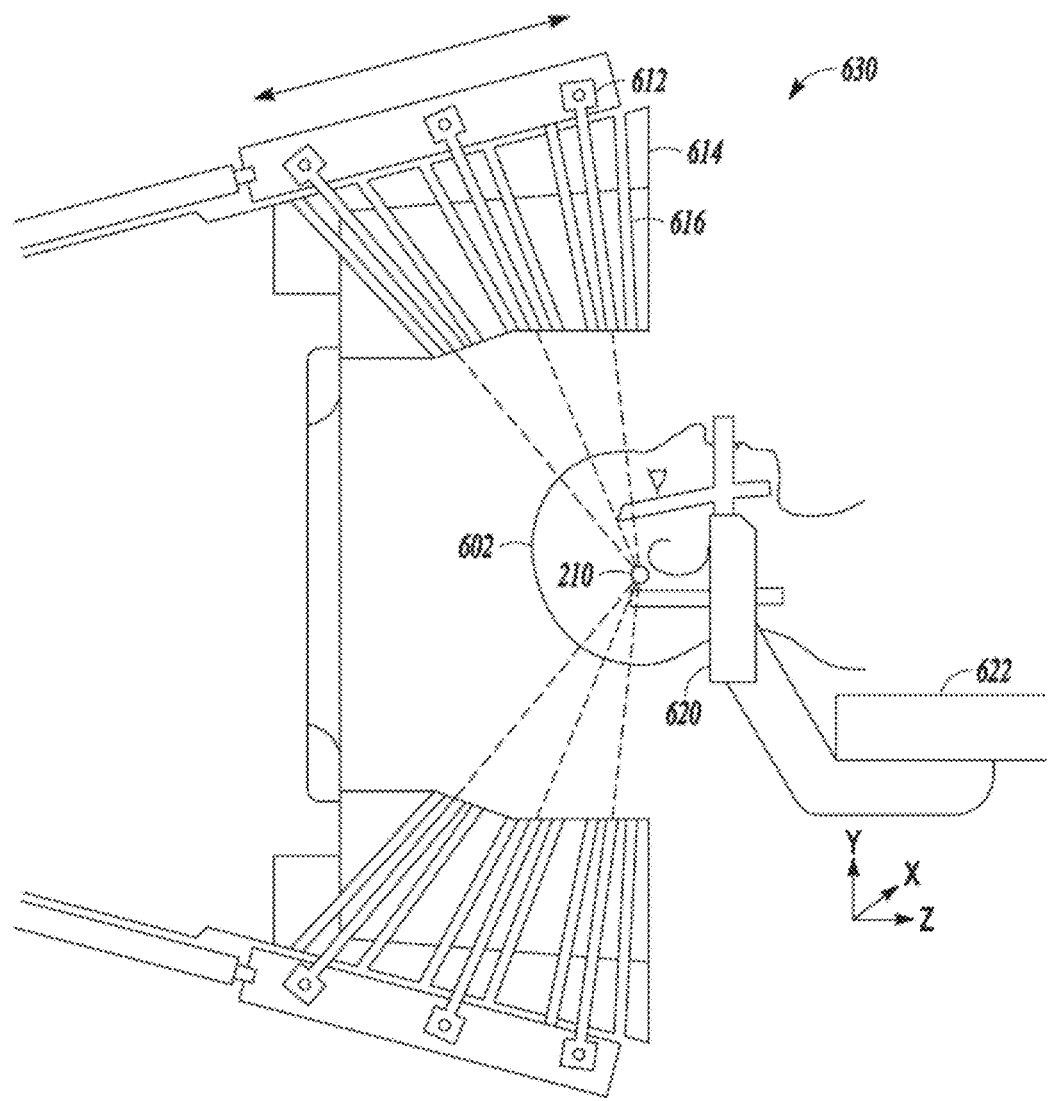
FIG. 6 illustrates an example Gamma Knife radiation therapy system, according to some embodiments of the present disclosure.

FIG. 6 illustrates an embodiment of another type of radiotherapy device 630 (e.g., a Leksell Gamma Knife), according to some embodiments 0f the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

In some examples, the image processing device 112 implements a dose processing device. The dose processing device can compute a measure of BED for one or more prior radiotherapy treatment session. For example, the dose processing device can receive or access dose information representing a dose distribution delivered during a first radiotherapy treatment fraction. The dose distribution can be received from the radiotherapy treatment device used to treat a given patient. The received dose distribution can be different from what was actually prescribed by the radiotherapy treatment plan for treating the particular type of tumor or target.

In some examples, an operator can receive a BED measure, one or more images of the patient and a prescribed dose to be delivered during the first radiotherapy treatment fraction. Prior to instructing the radiotherapy treatment device to begin delivering the first radiotherapy treatment fraction, the operator can make adjustments to the prescribed dose based on the BED measure and the one or more images. For example, the operator can increase or decrease the dose distribution based on the distance between the tumor or target and the OAR.

In some examples, the radiotherapy device can deliver the first radiotherapy treatment fraction to the patient (e.g., after adjusting the dose distribution). The dose processing device can then update the measure of BED in accordance with Equation 1 based on the dose distribution delivered during the first radiotherapy treatment fraction. For example, the dose processing device can determine a type of tumor cell or target being treated and access a database to obtain first and second constants representing biological dose effects of delivering radiotherapy dose distribution to the type of tumor cell. The dose processing device, can, for example, obtain the p and a constants from the database based on the type f tumor cell or target.

The measure of BED can take into account the current dose distribution delivered during the first radiotherapy treatment fraction and the dose distribution delivered during prior radiotherapy treatment fractions. Namely, the dose processing device can store a record associated with the patient being treated. The dose processing device can generate a list of radiotherapy treatment fractions in the record and associate the actual physical dose distribution delivered to the patient during each respective radiotherapy treatment fraction. The dose processing device, in computing the measure of BED for a most recent radiotherapy treatment fraction, obtains the first and second constants and the list of actual physical dose distributions delivered during each particular previous radiotherapy treatment fraction for the patient. The dose processing device then computes a first value representing a sum of all of the retrieved actual physical dose distributions and the currant dose distribution of the latest radiotherapy treatment fraction. The dose processing device also computes a second value representing a multiplication of a ratio of the first and second constants by a sum of the square of all of the retrieved actual physical dose distributions and the current dose distribution of the latest radiotherapy treatment fraction. The dose processing device computes the measure of BED as a sum of the first and second values. In this way, the BED is a second order function of a plurality of doses delivered across a plurality of radiotherapy treatment fractions.

In some examples, the dose processing device can present this current measure of BED to a dosimetrist or operator prior to delivery of a subsequent radiotherapy treatment fraction to the patient. The dosimetrist or operator can perform an isotoxic planning process or the dose processing device can perform an automated isotoxic planning process to adjust a prescribed dose delivered during the subsequent radiotherapy treatment fraction based on the current measure of BED. After the subsequent radiotherapy treatment fraction is delivered the measure of BED is again updated and the record associated with the patient is updated to reflect the actual dose distribution delivered to the patient during the subsequent radiotherapy treatment fraction for use in computing future measures of BED.

In some examples, the dose processing device can compute a total survival fraction of tumor cells based on the computed measure of BED. The total survival fraction can also be used to adjust a dose distribution delivered during a subsequent treatment fraction. The total survival fraction can be computed in accordance with Equation 2 below:

$$\exp[-\alpha\{BED\}]  \quad \text{Equation 2}$$

where $\alpha$ represents the second constant of the BED formulation defined by Equation 1 and exp is an exponential function.

In some examples, the computed BED can be stored as part of training data used to train one or more machine learning techniques, as explained below. For example, the training data can be generated and stored representing different types of tumors or targets and specified actual dose distributions delivered across a set of radiotherapy treatment fractions. As each radiotherapy treatment fraction is delivered, the actual dose distribution for that radiotherapy treatment fraction is received, stored in the training data among a plurality of other dose distributions delivered to the patient and the BED computed according to Equation 1. The BED that is stored can be the ground truth BED that is computed for a particular type of target or tumor and a set of radiotherapy treatment fraction dose distributions.

In some examples, the dose processing device can receive a dose distribution for an upcoming (or past) radiotherapy treatment fraction and a type of target being treated. The dose processing device can apply a trained machine learning technique to the dose distribution and the type of target being treated to estimate the BED for the upcoming (or past) radiotherapy treatment fraction. Based on the estimated BED, an operator or the dose processing device can adjust the dose distribution that will be delivered during the radiotherapy treatment fraction or a subsequent radiotherapy treatment fraction. For example, the dose processing device can implement a plurality of machine learning techniques. Each of the machine learning techniques (e.g., neural networks) can be trained to estimate or predict a BED for a given dose distribution associated with a different target type or tumor cell type. The dose processing device can select a machine learning technique associated with a target type of a patient. The dose processing device can apply the prescribed or adjusted dose to the selected machine learning technique to estimate the BED for the prescribed or adjusted dose. The estimated BED can then be used in an isotoxic planning process or to perform quality assurance on computed BED measures.

In some examples, after delivery of a radiotherapy treatment fraction, the actual dose distribution is obtained together with past dose distributions from prior radiotherapy treatment fractions. The dose processing device can compute the BED based on Equation 1 and the dose distributions of the current and prior radiotherapy treatment fraction. The dose processing device can also apply a machine learning technique on the current dose distribution (the actual dose distribution applied by the radiotherapy treatment fraction or the dose distribution specified in the radiotherapy treatment plan for the radiotherapy treatment fraction) to estimate the BED for the radiotherapy treatment fraction. The dose processing device can compare the computed BED based on Equation 1 with the estimated BED to perform a quality assurance check. In some cases, the dose processing device can compute a deviation or difference between the computed BED and the estimated BED and compare the difference to a threshold. In response to determining that the difference is greater than the threshold, the dose processing device can alert an operator to adjust the dose distribution for a future radiotherapy treatment fraction.

Figure 7:
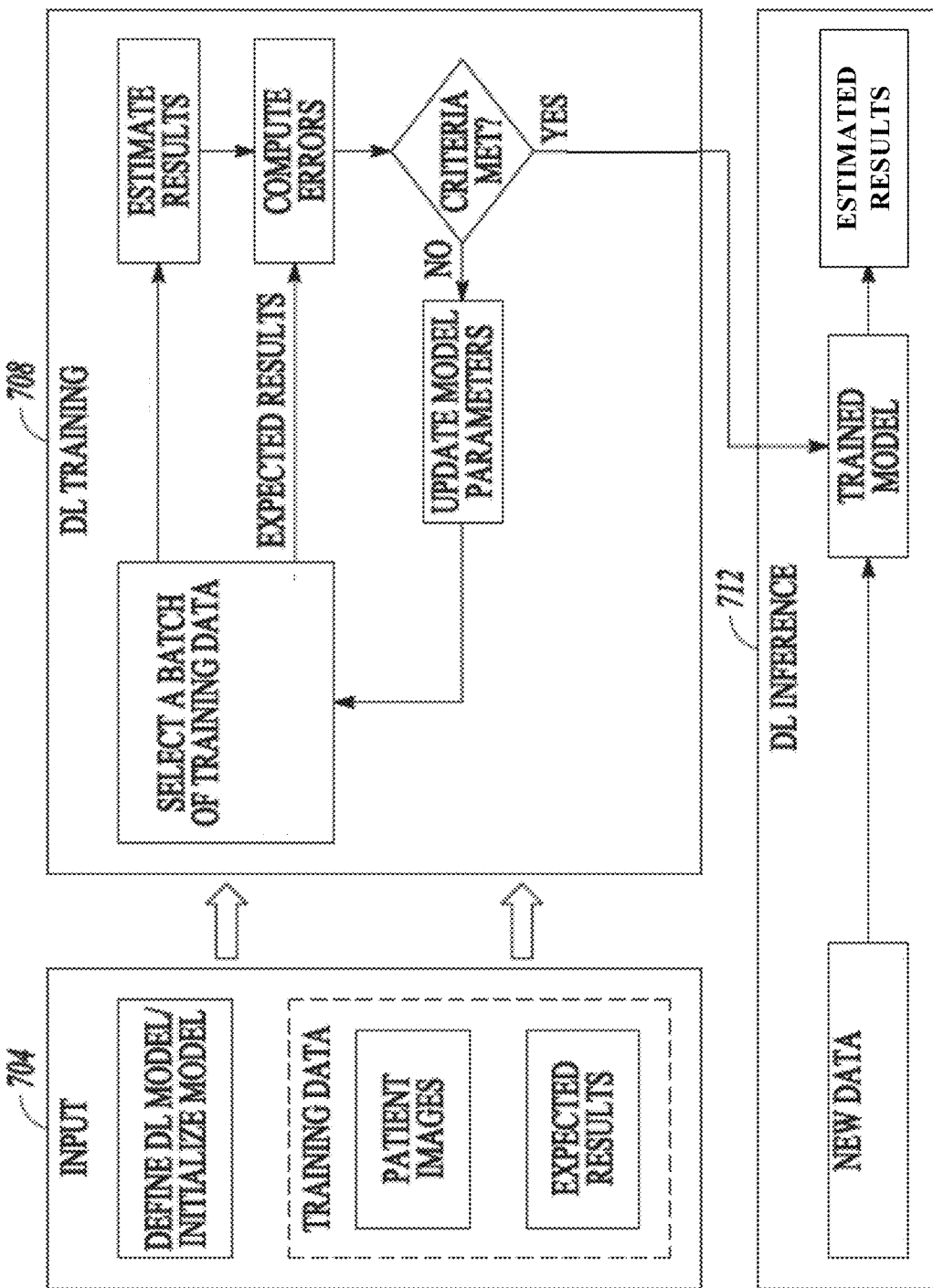
FIG. 7 illustrates an example flow diagram for deep learning, according to some embodiments of the present disclosure.

FIG. 7 illustrates an example flow diagram for deep learning, where a deep learning model (or a machine learning model), such as a deep convolutional neural network (DCNN), autoencoder neural network, or variational autoencoder neural network, can be trained and used to generate predictions or estimations of BED based on one or more training data, such as training dose distributions and tumor/target types. After the DCNN is trained, the DCNN can be applied to a new dose distribution (or collection of dose distributions) to estimate BED the new dose distribution.

Inputs 704 can include a defined deep learning model (which can include one or more sub-networks or one or more individual and independent machine learning models) having an initial set of values and training data. The training data can include multiple training dose distributions for different types of targets and corresponding ground truth BED measurements.

The deep learning model can include one or more neural networks (referred to as sub-networks), such as a DCNN or autoencoder neural network. The deep learning network can be trained on the training data to establish a relationship between a given set of the dose distributions for a given target type and the corresponding ground truth BED measurement. In some examples, training data can be generated by applying the given set of the dose distributions to Equation 1 to obtain the corresponding ground truth BED measurement of the given set of the dose distributions. In this way, the DCNN can be applied to a set of dose distributions or one dose distribution associated with a particular target type to generate an estimation of BED for the target type and the dose distribution. This estimation can be compared (e.g., for quality assurance purposes) to an actual measured BED for a treatment fraction or set of treatment fractions to ensure accuracy of the measured BED.

During training of deep learning (DL) model 708, a batch of training data can be selected from the training data of known patients or of a patient undergoing radiotherapy. The DL model 708 (e.g., the neural network) is applied to the batch of training data to generate an estimate of BED. The ground truth BED associated with the batch of training data is retrieved (e.g., the BED that has been calculated using Equation 1 based on a set of dose distributions associated with a set of treatment fractions). A deviation is computed based on a comparison of the ground truth BED and the estimated BED and parameters of the DL model 708 (e.g., the neural network) are updated based on the computed deviation.

The errors or result of computing the deviation (loss) can be used during a procedure called backpropagation to update the parameters of the deep learning network (e.g., layer node weights and biases of each or of certain sub-networks of the model 708), in order to reduce or minimize errors during subsequent trials. The errors or result of computing the deviation can be compared to predetermined criteria, such as proceeding to a sustained minimum for a specified number of training iterations. If the errors or result of computing the loss function do not satisfy the predetermined criteria, then model parameters of the deep learning model 708 can be updated using backpropagation, and another batch of training data can be selected from the other sets of training data (of the same patient or other patients) and expected results for another iteration of deep learning model training. If the errors or result of computing the loss function satisfy the predetermined criteria, then the training can be ended, and the trained model 708 can then be used during a deep learning testing or inference stage 712 to generate BED estimates for subsequently received dose distributions.

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, such as a memory device, and the training can be halted. If the stopping criteria are not satisfied, then the training can continue by obtaining another batch of training data from the same training subject or another training subject. In an embodiment, the stopping criteria can include a value of the iteration index (e.g., the stopping criteria can include whether the iteration index is greater than or equal to a determined maximum number of iterations). The steps recited above for training the DL model 708 can be repeated for each set or batch of training data associated with the same or different patient and/or region of interest.

After the DL model 708 is trained, the DL model 708 is applied to a new dose distribution (data sample for an upcoming radiotherapy treatment fraction or dose distributions for the entire set of treatment fractions associated with a patient) to generate an estimated BED for the new dose distribution associated with a particular type of tumor or target. If a difference between an estimated BED and a measured BED that is computed according to Equation 1 (such as based on prior dose distributions of prior radiotherapy treatment fractions) exceeds a threshold, the output of DL model 708 can be applied to update or control delivery of the radiotherapy treatment plan, such as by modifying the dose distribution for the upcoming radiotherapy treatment fraction.

Figure 8:
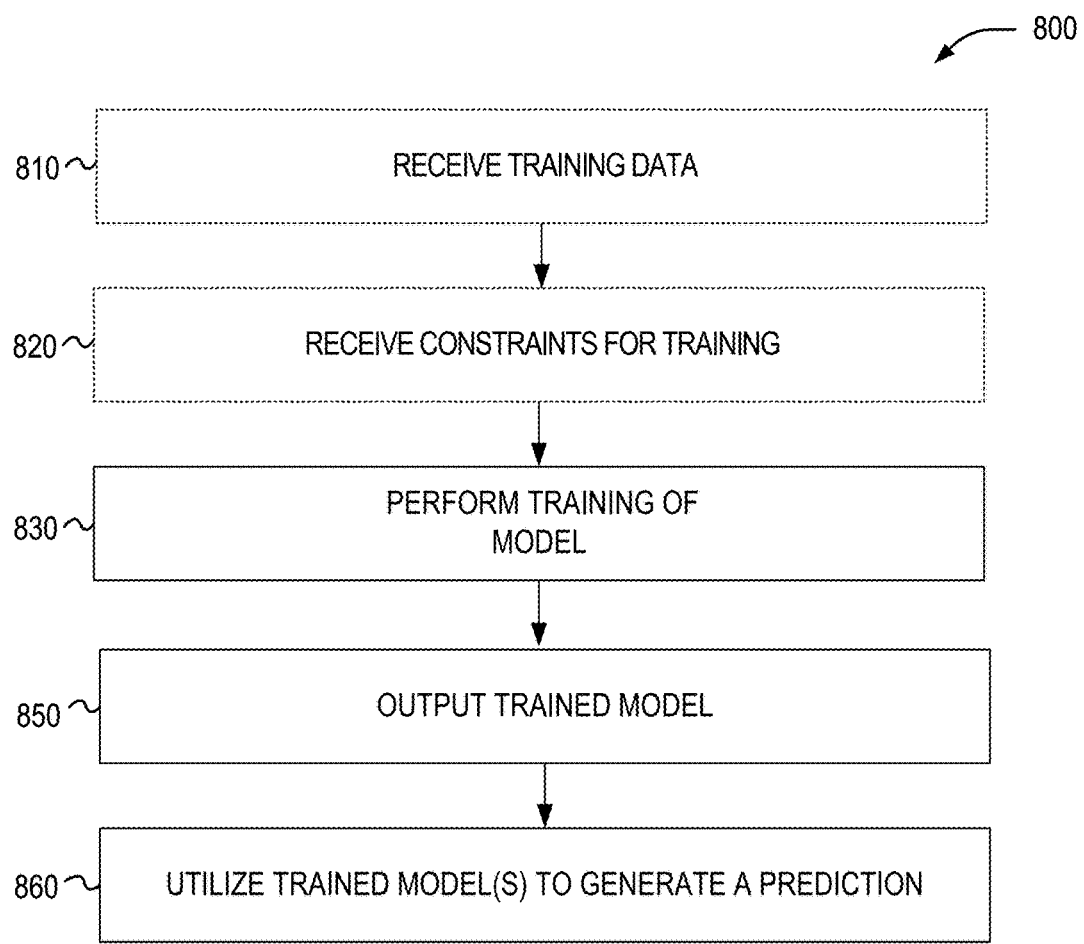
FIG. 8 illustrates an example data flow for training and use of a machine learning model, according to some embodiments of the present disclosure.

FIG. 8 is a flowchart illustrating example operations of the image processing device 112 in performing process 800, according to example embodiments. The process 800 may be embodied in computer-readable instructions for execution by one or more processors such that the operations of the process 800 May be performed in part or in whole by the functional components of the image processing device 112; accordingly, the process 800 is described below by way of example with reference thereto. However, in other embodiments, at least some of the operations of the process 800 may be deployed on various other hardware configurations. The process 800 is therefore not intended to be limited to the image processing device 112 (e.g., dose processing device) and can be implemented in whole, or in part, by any other component. Some or all of the operations of process 1100 can be in parallel, out of order, or entirely omitted.

At operation 810, image processing device 112 receives training data (paired dose distributions and ground truth BED measurements). For example, image processing device 112 receives training data, which may include paired training data sets (e.g., input-output training pairs).

At operation 820, image processing device 112 receives one or more cost functions for training the model.

At operation 830, image processing device 112 performs training of the model based on the received training data and one or more cost functions.

At operation 850, image processing device 112 outputs the trained model.

At operation 860, image processing device 112 utilizes the trained model to generate a prediction of a BED measurement based on an input dose distribution.

Figure 9A:
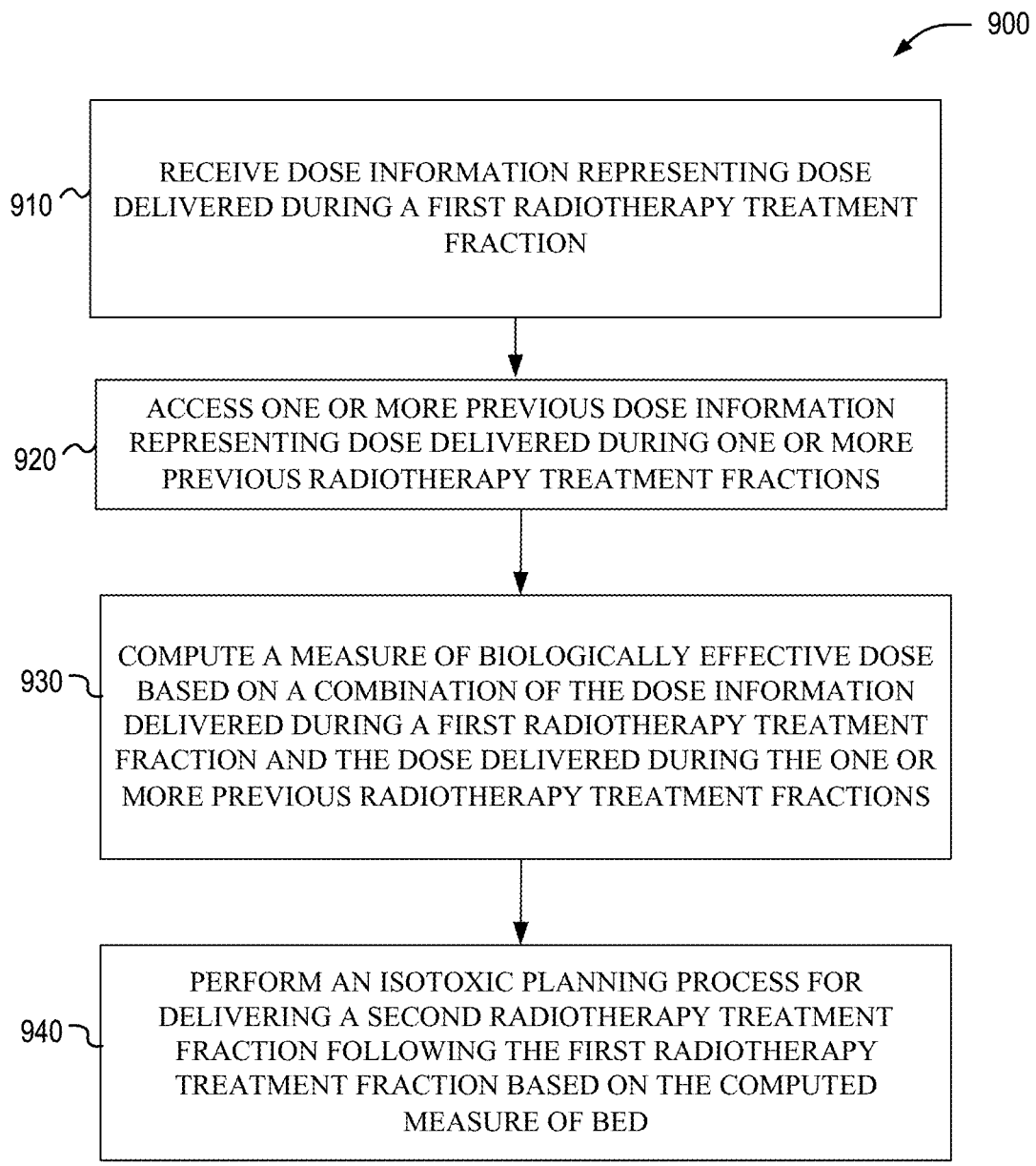
FIGS. 9A and 9B illustrate processes for computing biologically effective dose (BED), according to some embodiments of the present disclosure.

FIG. 9A is a flowchart illustrating example operations of the image processing device 112 in performing process 900, according to example embodiments. The process 900 may be embodied in computer-readable instructions for execution by one or more processors such that the operations of the process 900 may be performed in part or in whole by the functional components of the image processing device 112 accordingly, the process 900 is described below by way of example with reference thereto. However, in other embodiments, at least some of the operations of the process 900 may be deployed on various other hardware configurations. The process 900 is therefore not intended to be limited to the image processing device 112 and can be implemented in whole, or in part, by any other component. Some or all of the operations of process 900 can be in parallel, out of order, or entirely omitted.

At operation 910, image processing device 112 receives dose information representing dose delivered during a first radiotherapy treatment fraction, as discussed above.

At operation 920, image processing device 112 accesses one or more previous dose information representing dose delivered during one or more previous radiotherapy treatment fractions, as discussed above.

At operation 930, image processing device 112 computes a measure of BED based on a combination of the dose information delivered during a first radiotherapy treatment fraction and the dose delivered during the one or more previous radiotherapy treatment fractions, as discussed above.

At operation 940, image processing device 112 performs an isotoxic planning process for delivering a second radiotherapy treatment fraction following the first radiotherapy treatment fraction based on the computed measure of BED, as discussed above.

Figure 9B:
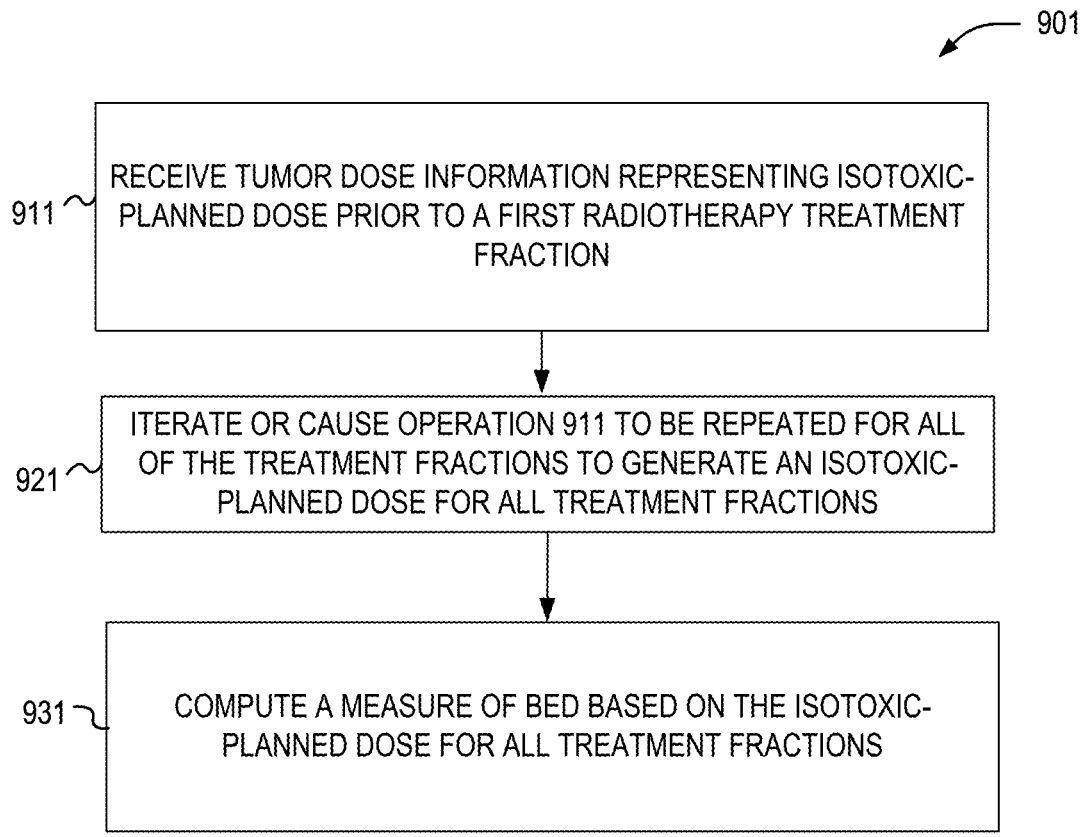

FIG. 9B is a flowchart illustrating example operations of the image processing device 112 in performing process 901, according to example embodiments. The process 901 may be embodied in computer-readable instructions for execution by one or more processors such that the operations of the process 901 may be performed in part or in whole by the functional components of the image processing device 112 accordingly, the process 901 is described below by way of example with reference thereto. However, in other embodiments, at least some of the operations of the process 901 may be deployed on various other hardware configurations. The process 901 is therefore not intended to be limited to the image processing device 112 and can be implemented in whole, or in part, by any other component. Some or all of the operations of process 901 can be in parallel, out of order, or entirely omitted.

At operation 911, image processing device 112 receives tumor dose information representing isotoxic-planned dose prior to a first radiotherapy treatment fraction, as discussed above.

At operation 921, image processing device 112 iterates or causes operation 911 to be repeated for all of the treatment fractions to generate an isotoxic-planned dose for all treatment fractions, as discussed above.

At operation 931, image processing device 112 computes a measure of BED by applying the isotoxic-planned dose for all treatment fractions to Equation 1, as discussed above.

Figure 10:
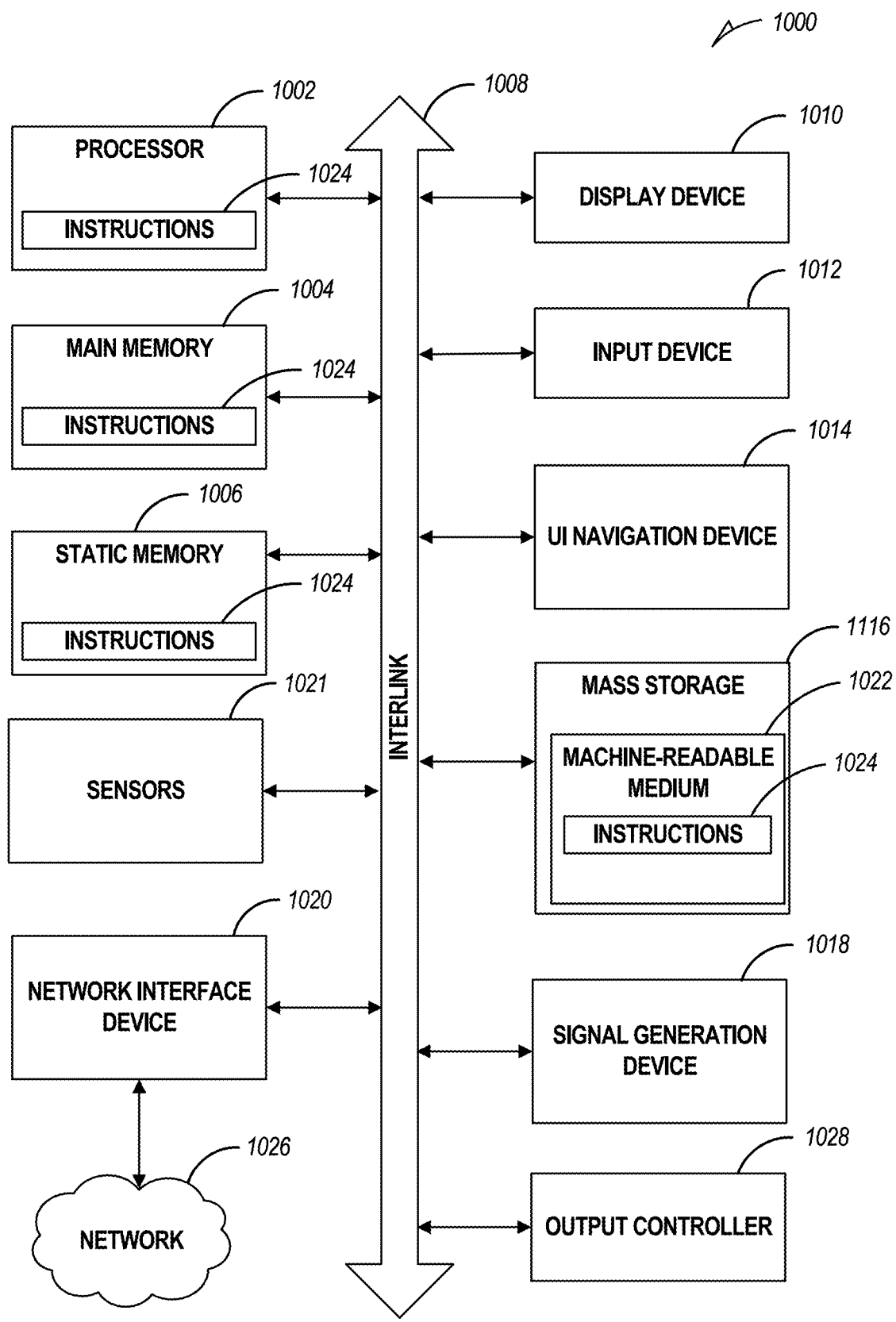
FIG. 10 illustrates an example block diagram of a machine on which one or more of the methods as discussed herein can be implemented.

FIG. 10 illustrates a block diagram of an embodiment of a machine 1000 on which one or more of the methods as discussed herein can be implemented. In one or more embodiments, one or more items of the image processing device 112 can be implemented by the machine 1000. In alternative embodiments, the machine 1000 operates as a standalone device or may be connected (e.g., networked) to other machines. In one or more embodiments, the image processing device 112 can include one or more of the items of the machine 1000. In a networked deployment, the machine 1000 may operate in the capacity of a server or a client machine in server-client network environment, or as a peer machine in a peer-to-peer for distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 includes processor 1002 (e.g., a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. The machine 1000 (e.g., computer system) may further include a video display unit 1010 (e.g., a liquid crystal display (LCD) or a cathode ray tube (CRT)). The machine 1000 also includes an alphanumeric input device 1012 (e.g., a keyboard), a user interface (UI) navigation device 1014 (e.g., a mouse), a disk drive or mass storage unit 1016, a signal generation device 1018 (e.g., a speaker), and a network interface device 1020.

The disk drive or mass storage unit 1016 includes a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated includes an output controller 1028. The output controller 1028 manages data flow to/from the machine 1000. The output controller 1028 is sometimes called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and slash memory devices; magnetic disks such as internal hard disks and removable disks magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

ADDITIONAL NOTES

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that elements after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., ROMs), EPROMS, EEPROMS, or any type of media suitable for storing electronic instructions, and the like. Such computer-readable storage medium may be coupled to a computer system bus to be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, Compute Unified Device Architecture (CUDA), C, C++, Java, Python, and the like; and using standard machine learning/deep learning library (or API), such as tensorflow, torch and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are example embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A system comprising:
   a memory; and
   one or more processors that, when executing instructions stored in the memory, are configured to perform operations comprising:
   receiving dose information representing delivery of a dose distribution to a target corresponding to a first radiotherapy treatment fraction;
   determining a type of tumor associated with the target;
   selecting a machine learning technique from a plurality of machine learning techniques based on the determined type of tumor associated with the target, a first of the plurality of machine learning techniques trained to estimate a measure of biologically effective dose (BED) associated with a first type of tumor, and a second of the plurality of machine learning techniques trained to estimate a measure of BED associated with a second type of tumor;
   applying the selected machine learning technique to the dose information to predict a measure of BED, the selected machine learning technique trained to establish a relationship between a set of prior dose distributions delivered for the determined type of tumor and one or more ground truth BED measurements, the selected machine learning technique trained by:
      obtaining a set of training data comprising a set of training dose distributions and a ground truth measure of BED;
      applying the selected machine learning technique to the set of training dose distributions to predict a training measure of BED;
      computing a deviation between the predicted training measure of BED and the ground truth measure of BED; and
      updating one or more parameters of the selected machine learning technique based on the deviation; and
   performing an isotoxic planning process based on the predicted measure of BED.

2. The system of claim 1, wherein the operations further comprise:
   storing a plurality of machine learning techniques each associated with a different target type of tumor and configured to predict BED for the associated target type.

3. The system of claim 1, wherein the operations comprise:
   combining one or more accumulated sets of training dose distributions and one or more adjusted sum of squares of the set of training dose distributions into the ground truth measure of BED to associate the ground truth measure of BED with the set of training dose distributions.

4. The system of claim 1, wherein the operations further comprise:
   computing a measured BED by:

accumulating a plurality of doses delivered across a plurality of radiotherapy treatment fractions into a first value, the plurality of radiotherapy treatment fractions comprising the first radiotherapy treatment fraction;

accumulating an adjusted sum of squares of the plurality of doses; and combining the accumulated plurality of doses and the adjusted sum of squares of the plurality of doses into the measure of BED, and comparing the measured BED to the predicted measure of BED.

5. The system of claim 4, wherein the operations further comprise:

computing a difference between the measured BED to the predicted measure of BED;

comparing the difference to a threshold; and controlling delivery of a radiotherapy treatment plan based on a result of comparing the difference to the threshold.

6. The system of claim 1, wherein the set of training data is generated by:

obtaining the set of training dose distributions associated with multiple radiotherapy treatment fractions;

accumulating the set of training dose distributions into a first value;

accumulating an adjusted sum of squares of the set of training dose distributions;

combining the accumulated set of training dose distributions and the adjusted sum of squares of the set of training dose distributions into the ground truth measure of BED; and associating the ground truth measure of BED with the set of training dose distributions.

7. A system comprising:

a memory; and one or more processors that, when executing instructions stored in the memory, are configured to perform operations comprising:

receiving dose information representing dose delivered during a first radiotherapy treatment fraction;

accessing one or more previous dose information representing dose delivered during one or more previous radiotherapy treatment fractions;

selecting a machine learning technique from a plurality of machine learning techniques based on a determined type of tumor associated with a target, a first of the plurality of machine learning techniques trained to estimate a measure of biologically effective dose (BED) associated with a first type of tumor, and a second of the plurality of machine learning techniques trained to estimate a measure of BED associated with a second type of tumor;

computing, by the selected machine learning technique, a measure of BED based on a combination of the dose information delivered during a first radiotherapy treatment fraction and the dose delivered during the one or more previous radiotherapy treatment fractions, the selected machine learning technique trained by:

obtaining a set of training data comprising a set of training dose distributions and a ground truth measure of BED;

applying the selected machine learning technique to the set of training dose distributions to predict a training measure of BED;

computing a deviation between the predicted training measure of BED and the ground truth measure of BED; and updating one or more parameters of the selected machine learning technique based on the deviation; and performing an isotoxic planning process for delivering a second radiotherapy treatment fraction following the first radiotherapy treatment fraction based on the computed measure of BED.

8. The system of claim 7, wherein the one or more previous radiotherapy treatment fractions were delivered prior to the first radiotherapy treatment fraction.

9. The system of claim 7, wherein the operations further comprise:

computing a total survival fraction of tumor cells based on the computed measure of BED.

10. The system of claim 9, wherein the operations further comprise:

obtaining a first constant corresponding to a tumor cell associated with a patient being treated by the first radiotherapy treatment fraction; and computing the total survival fraction as an exponential of the first constant and the computed measure of BED.

11. The system of claim 7, wherein the operations further comprise:

accumulating a plurality of doses delivered across a plurality of radiotherapy treatment fractions into a first value, the plurality of radiotherapy treatment fractions comprising the first radiotherapy treatment fraction and the one or more previous radiotherapy treatment fractions;

accumulating an adjusted sum of squares of the plurality of doses; and combining the accumulated plurality of doses and the adjusted sum of squares of the plurality of doses into the measure of BED.

12. The system of claim 11, wherein the operations further comprise:

obtaining first and second constants corresponding to a tumor cell associated with a patient being treated by the first radiotherapy treatment fraction;

computing a ratio of the first and second constants; and multiplying the sum of squares of the plurality of doses by the ratio to compute the adjusted sum of squares of the plurality of doses.

13. The system of claim 7, wherein the operations further comprise:

presenting the measure of BED to an operator before delivery of the second radiotherapy treatment fraction.

14. The system of claim 13, wherein the operations further comprise:

receiving magnetic resonance imaging information associated with the second radiotherapy treatment fraction prior to delivery of the second radiotherapy treatment fraction;

computing, based on the magnetic resonance imaging information, a distance between a critical organ and a tumor cell associated with a patient being treated by the second radiotherapy treatment fraction; and setting a dose to be delivered during the second radiotherapy treatment fraction based on the distance and the measure of BED.

15. The system of claim 13, wherein the operations further comprise:

adjusting the set dose during delivery of the second radiotherapy treatment fraction; and updating the measure of BED based on the adjusted set dose delivered during the second radiotherapy treatment fraction.

16. The system of claim 7, wherein the measure of the BED comprises a second order function of a plurality of doses delivered across a plurality of radiotherapy treatment fractions.

17. The system of claim 7, wherein the measure of the BED is computed in accordance with:

$$BED=\Sigma d_i+(\beta/\alpha)\Sigma d_i^2$$

where BED is the measure of BED, $d_i$ represents dose delivered during a radiotherapy treatment fraction number i, $\beta$ and $\alpha$ represent respectively first and second constants associated with a tumor cell associated with a patient being treated by the first radiotherapy treatment fraction.

18. The system of claim 17, wherein a total survival fraction is computed in accordance with:

$$\exp[-\alpha\{BED\}]$$

where exp is an exponential function.

19. A method comprising:
receiving dose information representing dose delivered during a first radiotherapy treatment fraction;
accessing one or more previous dose information representing dose delivered during one or more previous radiotherapy treatment fractions;
selecting a machine learning technique from a plurality of machine learning techniques based on a determined type of tumor associated with a target, a first of the plurality of machine learning techniques trained to estimate a measure of biologically effective dose (BED) associated with a first type of tumor, and a second of the plurality of machine learning techniques trained to estimate a measure of BED associated with a second type of tumor:
computing, by the selected machine learning technique, a measure of BED based on a combination of the dose information delivered during a first radiotherapy treatment fraction and the dose delivered during the one or more previous radiotherapy treatment fractions, the selected machine learning technique trained by:
obtaining a set of training data comprising a set of training dose distributions and a ground truth measure of BED;
applying the selected machine learning technique to the set of training dose distributions to predict a training measure of BED;
computing a deviation between the predicted training measure of BED and the ground truth measure of BED; and
updating one or more parameters of the selected machine learning technique based on the deviation; and
performing an isotoxic planning process for delivering a second radiotherapy treatment fraction following the first radiotherapy treatment fraction based on the computed measure of BED.

20. The method of claim 19, wherein the one or more previous radiotherapy treatment fractions were delivered prior to the first radiotherapy treatment fraction.

21. The method of claim 19, further comprising:
computing a total survival fraction of tumor cells based on the computed measure of BED.

22. The method of claim 21, further comprising:
obtaining a first constant corresponding to a tumor cell associated with a patient being treated by the first radiotherapy treatment fraction;
computing the total survival fraction as an exponential of the first constant and the computed measure of BED.

23. The method of claim 19, further comprising:
accumulating a plurality of doses delivered across a plurality of radiotherapy treatment fractions into a first value, the plurality of radiotherapy treatment fractions comprising the first radiotherapy treatment fraction and the one or more previous radiotherapy treatment fractions;
accumulating an adjusted exponent of the plurality of doses; and
combining the accumulated plurality of doses and the adjusted exponent of the plurality of doses into the measure of BED.

24. The method of claim 23, further comprising:
obtaining first and second constants corresponding to a tumor cell associated with a patient being treated by the first radiotherapy treatment fraction;
computing a ratio of the first and second constants; and
multiplying the exponent of the plurality of doses by the ratio to compute the adjusted exponent of the plurality of doses.

25. A non-transitory computer readable medium comprising instructions that, when executed by one or more processors, configure the one or more processors to perform operations comprising:
receiving dose information representing dose delivered during a first radiotherapy treatment fraction;
accessing one or more previous dose information representing dose delivered during one or more previous radiotherapy treatment fractions;
selecting a machine learning technique from a plurality of machine learning techniques based on a determined type of tumor associated with a target, a first of the plurality of machine learning techniques trained to estimate a measure of biologically effective dose (BED) associated with a first type of tumor, and a second of the plurality of machine learning techniques trained to estimate a measure of BED associated with a second type of tumor:
computing, by the selected machine learning technique, a measure of BED based on a combination of the dose information delivered during a first radiotherapy treatment fraction and the dose delivered during the one or more previous radiotherapy treatment fractions, the selected machine learning technique trained by:
obtaining a set of training data comprising a set of training dose distributions and a ground truth measure of BED;
applying the selected machine learning technique to the set of training dose distributions to predict a training measure of BED;
computing a deviation between the predicted training measure of BED and the ground truth measure of BED; and
updating one or more parameters of the selected machine learning technique based on the deviation; and
performing an isotoxic planning process for delivering a second radiotherapy treatment fraction following the first radiotherapy treatment fraction based on the computed measure of BED.

26. The non-transitory computer readable medium of claim 25, wherein the one or more previous radiotherapy treatment fractions were delivered prior to the first radiotherapy treatment fraction.

27. The non-transitory computer readable medium of claim 25, wherein the operations further comprise:
   computing a total survival fraction of tumor cells based on the computed measure of BED.

28. The non-transitory computer readable medium of claim 27, wherein the operations further comprise:
   obtaining a first constant corresponding to a tumor cell associated with a patient being treated by the first radiotherapy treatment fraction; and
   computing the total survival fraction as an exponential of the first constant and the computed measure of BED.

\* \* \* \* \*

UNITED STATES PATENT AND TRADEMARK OFFICE
CERTIFICATE OF CORRECTION

PATENT NO. : 12,239,848 B2
APPLICATION NO. : 17/647968
DATED : March 4, 2025
INVENTOR(S) : Kiyoshi Yoda Page 1 of 1

It is certified that error appears in the above-identified patent and that said Letters Patent is hereby corrected as shown below:

In the Claims

In Column 28, Line 29, in Claim 1, delete "tumor:" and insert --tumor;-- therefor In Column 28, Line 57, in Claim 3, delete "claim 1." and insert --claim 1,-- therefor In Column 29, Line 9, in Claim 4, delete "BED," and insert --BED;-- therefor In Column 29, Line 9, in Claim 4, after "and", insert a linebreak In Column 29, Line 61, in Claim 7, delete "BED:" and insert --BED;-- therefor In Column 31, Line 35, in Claim 19, delete "tumor:" and insert --tumor;-- therefor In Column 32, Line 41, in Claim 25, delete "tumor:" and insert --tumor;-- therefor Signed and Sealed this
Thirtieth Day of September, 2025

John A. Squires
*Director of the United States Patent and Trademark Office*